United States Patent
Wong et al.

[11] Patent Number: 5,889,199
[45] Date of Patent: Mar. 30, 1999

[54] PORTABLE LEAK DETECTOR

[75] Inventors: Jacob Y. Wong, Goleta; Rudy W. Tietze, Santa Barbara, both of Calif.

[73] Assignee: Jaesent Inc., Goleta, Calif.

[21] Appl. No.: 904,050

[22] Filed: Jul. 31, 1997

Related U.S. Application Data

[63] Continuation-in-part of Ser. No. 855,174, May 13, 1997, Pat. No. 5,798,696.

[51] Int. Cl.⁶ .................. G01M 3/04; G01J 5/02
[52] U.S. Cl. .................. 73/40; 73/40.7; 250/343
[58] Field of Search ............ 73/40, 40.7; 250/343; 356/437

[56] References Cited

U.S. PATENT DOCUMENTS

| | | | |
|---|---|---|---|
| 3,645,127 | 2/1972 | Mongodin et al. | 73/40.7 |
| 4,507,558 | 3/1985 | Bonne | 250/345 |
| 5,055,690 | 10/1991 | Bonne | 250/343 |
| 5,170,064 | 12/1992 | Howe | 250/573 |
| 5,522,253 | 6/1996 | Knight | 73/23.34 |

*Primary Examiner*—Hezron Williams
*Assistant Examiner*—Jay L. Politzer
*Attorney, Agent, or Firm*—Daniel C. McKown

[57] ABSTRACT

A portable instrument for locating leaks through the wall of a chamber uses a non-dispersive infrared (NDIR) type detector. The instrument includes a gas sampling probe into which a continuous sample of gas is drawn by a small suction pump. The sample is conducted from the probe through a flexible conduit and through a gas sample chamber. The gas sample chamber contains a source of light or infrared radiation and a detector. A narrow pass band filter is interposed between the source and the detector, and the pass band of the filter is centered on an absorption band of the test gas that is to be detected. When the test gas is present, it absorbs some of the radiation. The detector produces an electrical signal representative of the concentration of the test gas. The detector is connected to a signal processing circuit that responds to rapid changes of test gas concentration but ignores slow changes in concentration, thereby reducing the false alarm rate. The sampling is done at atmospheric pressure and the system does not require a high vacuum system.

3 Claims, 5 Drawing Sheets

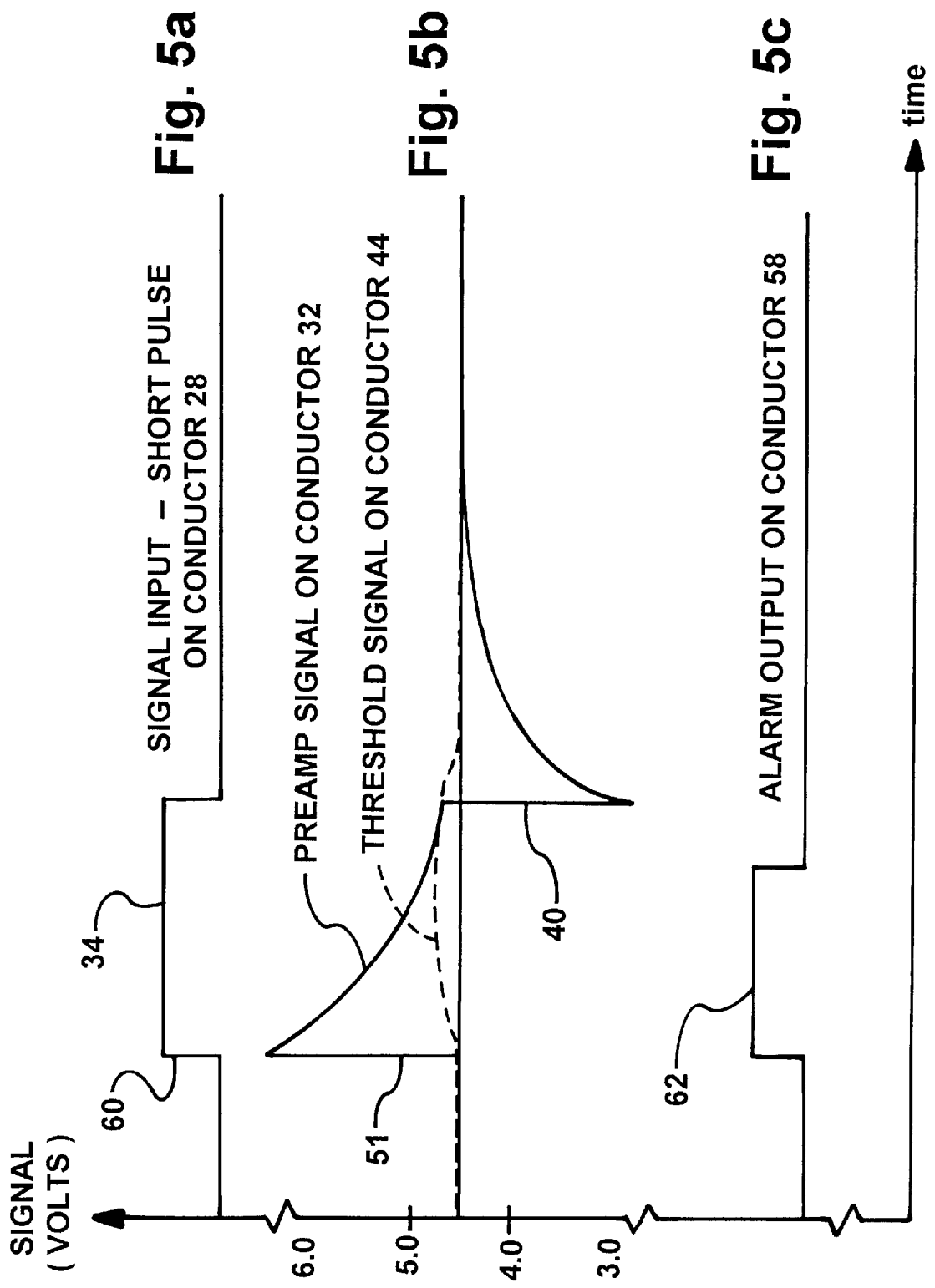

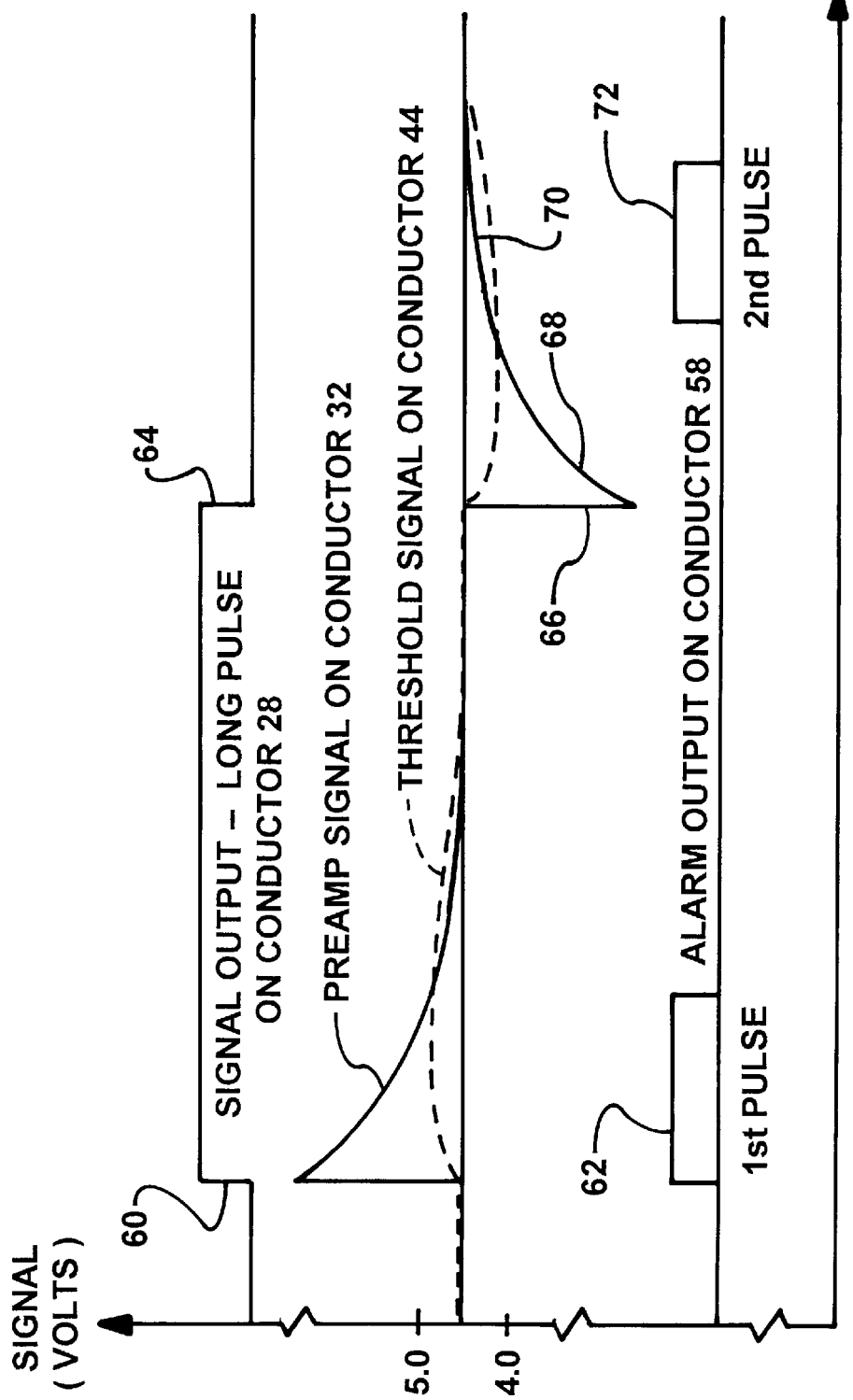

PORTABLE LEAK DETECTOR

CROSS REFERENCE TO RELATED APPLICATIONS

The present application is a continuation-in-part of U.S. application Ser. No. 08/855,174, now U.S. Pat. No. 5,798, 696 filed May 13, 1997 for TIRE PUNCTURE LOCATOR. The disclosure of that application is incorporated herein by reference to avoid unnecessary repetition of background material.

STATEMENT RE FEDERALLY SPONSORED RESEARCH OR DEVELOPMENT

Not applicable.

REFERENCE TO A "MICROFICHE APPENDIX"

Not applicable.

BACKGROUND OF THE INVENTION

1. Field of the Invention

The present invention is in the field of instrumentation and specifically relates to apparatus and method for locating regions in the external wall of a chamber through which a gas, vapor or liquid is leaking.

2. The Prior Art

The helium leak detection technique remains today, many decades after its invention, unequivocally as the best technique ever devised for leak detection, especially for detecting very small leaks or leaks that require quantification in terms of leak rate. The art of helium leak detection is well developed, and the success of the technique results from the ability of helium to penetrate very small passages and from the ability of the mass spectrometer detector to sense extremely small quantities of helium.

The heart of the helium leak detector is the mass spectrometer. A typical mass spectrometer consists of an evacuated chamber into which a gas sample, which may include helium, is drawn. The sample is drawn transversely through an energetic electron beam that flows from a negatively charged filament to a positively charged collector plate. The electron beam knocks electrons from the molecules of the sample gas, whereby the molecules become positively charged ions. These ions are accelerated by an electric field and then passed between the poles of a strong magnet which causes the ions to follow curved paths. The radius of the curved path depends on the mass of the ion and on the strength of the magnetic field. For a particular magnetic field strength, helium ions will pass through a narrow slit in a plate and impinge on a detector, while ions of other masses will miss the slit and will fall on the plate and will not be detected. In this way the mass spectrometer selectively responds to the presence of helium molecules in the evacuated chamber.

In U.S. Pat. No. 4,459,844 issued Jul. 17, 1984 Burkhart describes three major methods of using a helium leak detector to find leaks through the wall of a chamber that is being tested. In the first method, the chamber is placed in communication with a mass spectrometer. Next, the chamber is evacuated and thereafter helium gas is applied to selected regions on the exterior of the chamber. The mass spectrometer operates in high vacuum, and the minute amount of helium leaking into the chamber does not disturb the high vacuum.

In the second method, the chamber to be tested is filled and pressurized with helium and then placed in an evacuated chamber containing a mass spectrometer. The existence of a leak can be discovered, but not its location. The minute amount of helium leaking out of the chamber being tested does not disturb the high vacuum in the evacuated chamber.

The helium leak detector is the leak detector of choice when these first and second methods are used. The vacuum pumps needed to evacuate the chambers also produce the vacuum necessary for operation of the mass spectrometer. The present invention is not intended for use in the first and second methods.

Instead, the present invention is intended for use in what Burkhart refers to as a third method, namely, sampling at atmospheric pressure. In Burkhart's third method, the chamber to be tested is filled and pressurized with helium gas. The chamber remains surrounded by air. A gas sampling probe is moved across the exterior surface of the chamber, drawing a sample of gas through the probe into a vacuum chamber that includes a mass spectrometer.

When the sampling is done at atmospheric pressure, certain shortcomings of the conventional helium leak detector are exposed and the comparative advantages of the present invention come into sharp focus.

The mass spectrometer must operate in a high vacuum; otherwise the filament will burn up and the ions will be scattered from their proper trajectories.

To maintain the necessary high vacuum requires a mechanical roughing pump, a cold trap, and a molecular diffusion pump, along with the ancillary instrumentation. In contrast, the present invention requires none of these cumbersome components.

Sampling at atmospheric pressure compromises the high vacuum required by the helium leak detector. To ameliorate this problem, the volumetric flow rate of the gas sampled must be severely curtailed, resulting in longer transport delays and reduced sensitivity.

As recognized by Gevaud et al. in U.S. Pat. No. 4,294,106 issued Oct. 13, 1981, the slow flow rate of the sampled gas combined with the transport delay of the sample in traveling from the gas sampling probe through a conduit and into the vacuum system implies that the gas sampling probe must be moved rather slowly across the surface of the chamber under test so that the leak alarm signal can be correlated with the position of the probe to permit accurate determination of the location of the leak.

Thus it is seen that the helium leak detector, notwithstanding its superiority when the sample is collected inside a vacuum chamber, has serious limitations for use in a portable system for sampling at atmospheric pressure. These limitations are the need for a high vacuum system and the limited sampling flow rate.

The present inventors recognized that these limitations of the helium leak detector could be avoided if a sensitive, quickly-responding gas detector could be found that does not need to be operated in a vacuum.

BRIEF SUMMARY OF THE INVENTION

The present invention is a system that uses a detector that has fast response and high sensitivity, and that does not need to be operated in a vacuum. Specifically, gas sensors of the non-dispersive infrared (NDIR) type are used in the present invention. Such sensors determine the concentration of test gas in a gas sample by measuring the absorption of infrared or visible radiation passing through the sample. Although NDIR-type gas sensors had been available since the mid-1950's, it was not until recently that one of the present inventors (Wong) first proposed the use of a wave guide sample chamber in U.S. Pat. No. 5,163,332 issued Nov. 17, 1992 that eliminates the necessity of having to use expensive infrared optics for the implementation of an NDIR-type gas sensor.

Unlike the mass spectrometer of the helium leak detector, the NDIR-type gas sensor does not require a vacuum, and this eliminates the need for mechanical roughing pumps, cold traps, and molecular diffusion pumps associated with the helium leak detector. As a result, the weight of the gas detector is reduced by approximately two orders of magnitude, and the cost is reduced by approximately three orders of magnitude. The resulting leak locating system, as described below, is extremely portable and rugged.

The novel features which are believed to be characteristic of the invention, both as to organization and method of operation, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

BRIEF DESCRIPTION OF THE SEVERAL VIEWS OF THE DRAWING

FIG. 5, including FIGS. 5a, 5b and 5c, is a graph showing various waveforms versus time in the circuit of FIG. 3 for a short or weak pulse input; and FIG. 6, including FIGS. 6a, 6b and 6c, is a graph showing various waveforms versus time in the circuit of FIG. 4 for a long or strong pulse input.

DETAILED DESCRIPTION OF THE INVENTION

Figure 1:
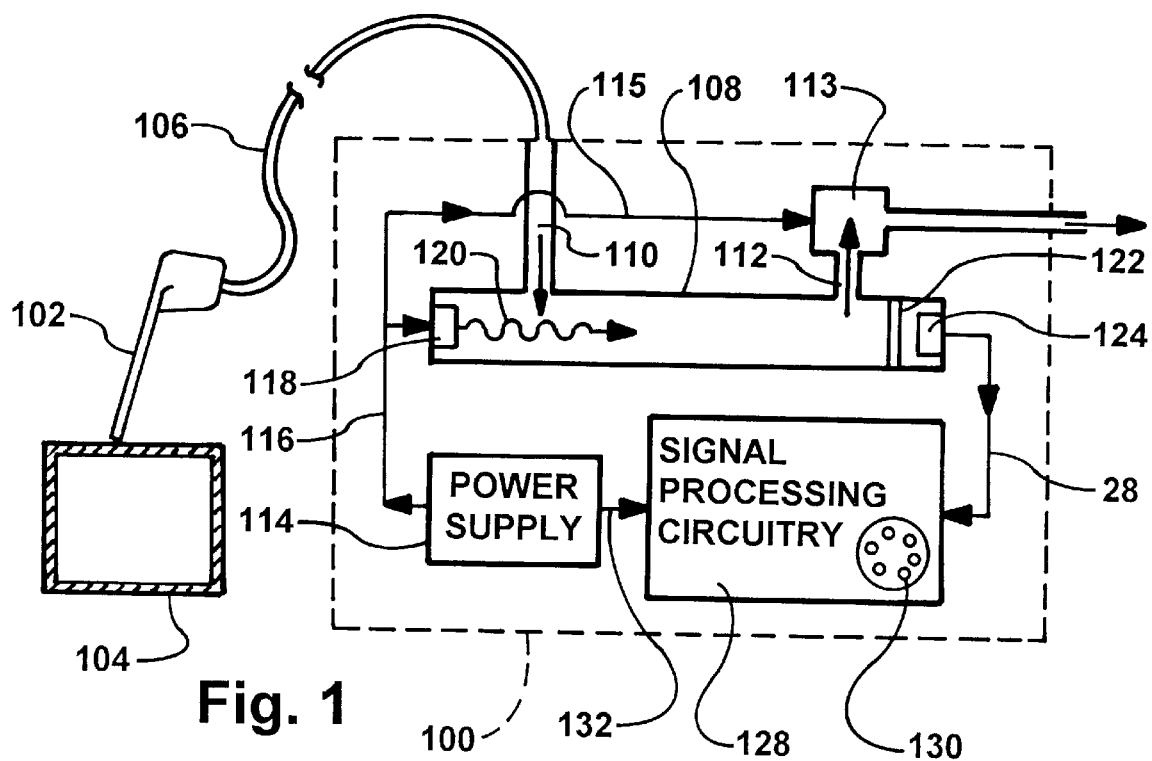
FIG. 1 is a diagram showing the major components of a leak locating system in a first preferred embodiment of the present invention.

FIG. 1 is a diagram showing the major components of a leak locating system in a first preferred embodiment of the invention. The chamber 104 that is to be tested is filled with a test gas and preferably is pressurized with the test gas so as to accelerate the leakage, if any, of the test gas from the chamber. The chamber is surrounded by an ambient gas which may be the air of the atmosphere, or, alternatively, the chamber 104 may be placed within a larger chamber so as to permit the chamber 104 to be surrounded by a chosen ambient gas other than air. In another embodiment, shown in FIG. 3 a localized region on the surface of the chamber may be flooded by a chosen ambient gas that temporarily displaces the air that otherwise would be present.

A continuous stream of sample gas is taken in through the gas sampling probe 102 which is connected to the leak detector 100 by means of a hose 106 or other suitable flexible conduit. A suction pump 113 draws the gas sample into the gas sample chamber 108 through the inlet port 110 and draws the gas out of the outlet port 112, discharging the gas sample into the atmosphere or into a bag.

A power supply 114 supplies electrical power to the signal processing circuitry 128 on the conductor 132, to the suction pump 113 on the conductor 115, and also supplies current on the conductor 116 to the incandescent lamp 118 or other radiation-producing component. In response to the current, the lamp 118 produces radiation in the infrared and the visible portions of the spectrum. The radiation 120 is guided by the cylindrical walls of the gas sample chamber 108 to the detector 124.

A narrow pass band filter 122 is interposed between the lamp 118 and the detector 124, so that the only radiation reaching the detector 124 is radiation having a wavelength equal to the wavelength passed by the filter 122. The center wavelength of the filter 122 is selected to coincide to the wavelength of a strong absorption band of the test gas, and it must also be a wavelength at which the ambient gas does not absorb radiation. Air is not necessarily the best choice for the ambient gas because air contains several gases each having absorption bands.

In accordance with the present invention, one may chose the test gas and the ambient gas so that a strong absorption band of the test gas coincides in wavelength with a portion of the spectrum in which the ambient gas does not absorb. When such a choice has been made, the wavelength of the filter 122 is chosen to coincide with the absorption band of the test gas. Likewise, the radiation source 118 must produce some radiation at the absorption band of the test gas. Once these choices have been made, the detector is unresponsive to the ambient gas, but strongly responds to the test gas, even when the test gas is mixed with the ambient gas.

The detector 124 produces an electrical signal on the conductor 28 representative of the concentration of the test gas in the gas sample chamber 108. The signal on the conductor 28 is applied to the signal processing circuitry 128, which is shown in greater detail in FIG. 4 and described below. The signal processing circuitry 128 operates an alarm 130 in response to certain changes in the concentration of the test gas.

Figure 2:
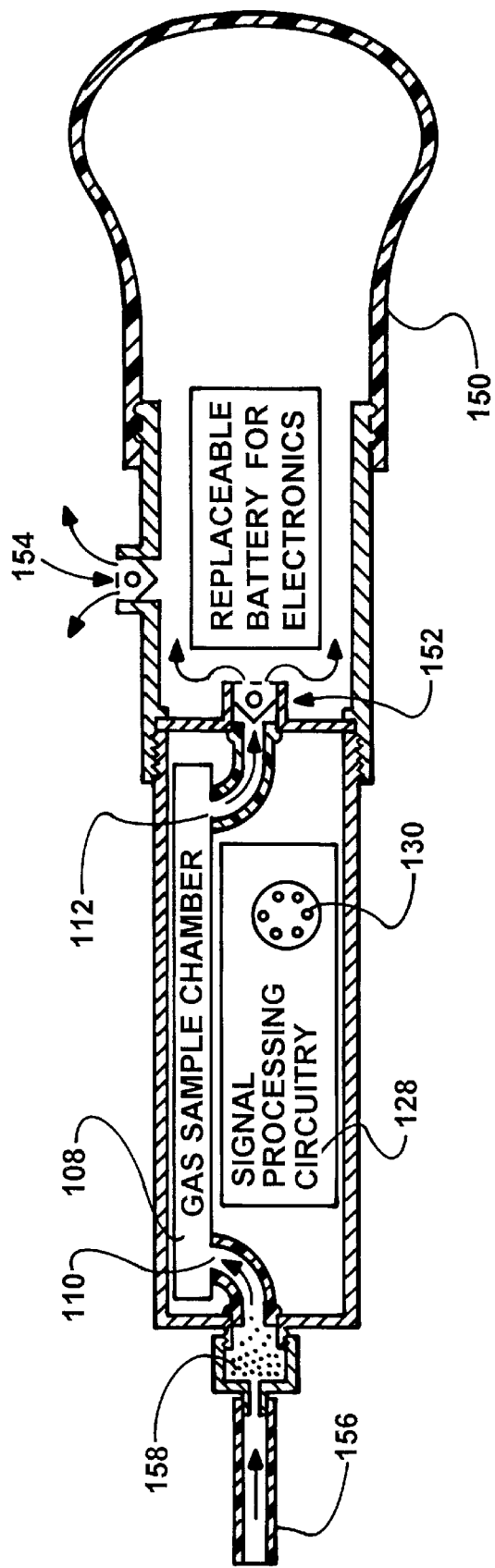
FIG. 2 is a diagram showing the mechanical layout of a hand-held manually-pumped leak locating system in accordance with a second preferred embodiment of the present invention.

FIG. 2 is a diagram showing the mechanical arrangement of the components in accordance with a second preferred embodiment of the invention. The invention is embodied as a hand-held manually-pumped instrument.

A rubber squeeze bulb 150 in association with an intake check valve 152 and a discharge check valve 154 permits the user to selectively create the mild suction required to draw in the gas sample through a very short length of flexible tubing 156 and a replaceable filter cartridge 158.

It is estimated that the instrument of FIG. 2 would be about the size of a flashlight and would probably weigh less than a flashlight. Because the gas sample chamber 108 is near the sample intake, transport delays are minimized.

Figure 3:
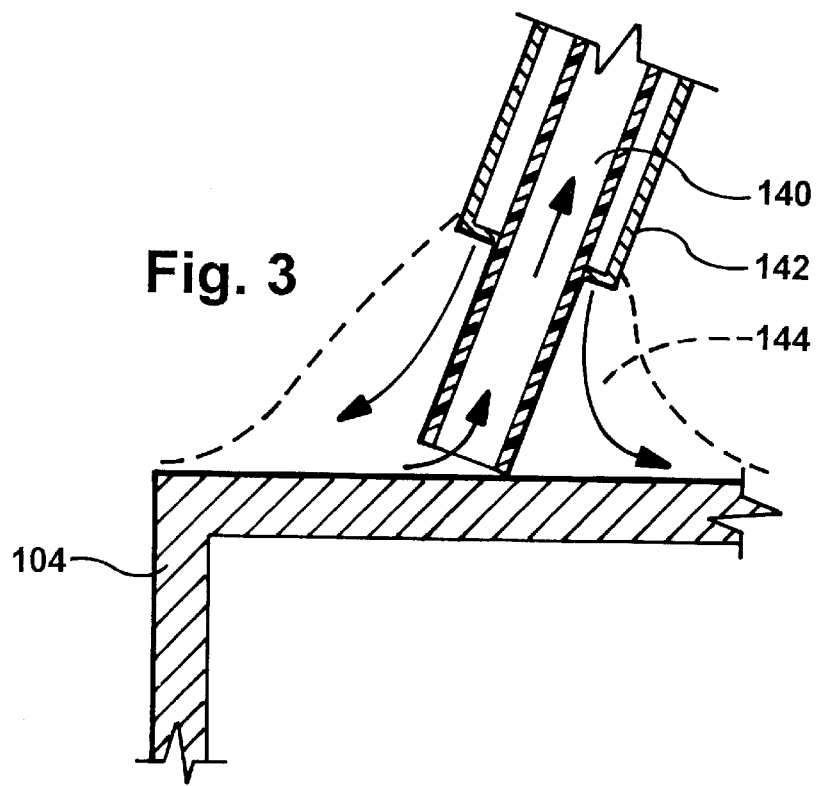
FIG. 3 is a diagram showing a probe for use with a leak detecting system.

If it is not practical to use air as the ambient gas, a gas sampling probe such as shown in FIG. 3 may be used. In that probe, the gas sample is taken in through an inner tube 140. The inner tube is surrounded by, but spaced from, a concentric outer tube 142, and a preferred ambient gas is continually discharged from the annular space between the inner tube and the outer tube. This discharged ambient gas blows away the air and creates a region 144 where only the chosen ambient gas is present.

Figure 4:
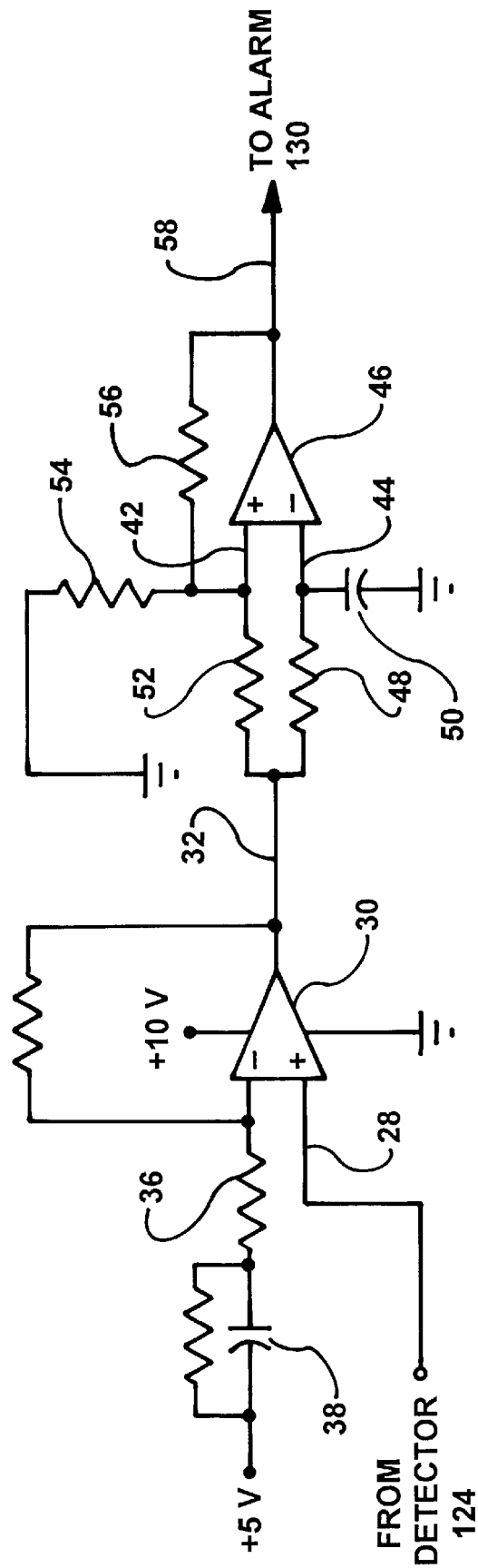
FIG. 4 is an electronic diagram of a signal processing circuit for use with a leak locating system.

FIG. 4 is an electronic diagram of a signal processing circuit for use with the leak detecting system of FIGS. 1 and 2.

In the preferred embodiment the lamp is not modulated, and its radiation causes the detector to produce a small steady signal of around 1 mV on the conductor 28 in the absence of test gas in the sample chamber. The preamplifier 30 amplifies this signal to a much higher level.

When test gas enters the sample chamber, it absorbs some of the infrared radiation, which causes the detector output on the conductor 28 to drop. The purpose of the signal processing circuit of FIG. 4 is to react to this drop in signal by producing an alarm output on the conductor 58.

In the preferred embodiment, the preamplifier 30 has a gain of about 200 for DC, and a higher gain of around 4,000 for AC. The detector polarity is such that a signal drop causes a positive signal change at the output of the preamplifier 30 on the conductor 32. The DC gain establishes a quiescent level of around 4.5V.

FIG. 5 shows some typical signals that help explain the operation of the circuit of FIG. 4. In FIG. 5a, the detector output is shown (inverted) as an idealized square pulse 34 to simplify the explanation. It is recognized that the real pulse shape will depend on the variation in time of the concentration of test gas in the sample chamber.

The high AC gain of the preamplifier 30 causes a quick change in the signal on conductor 32 in response to the incoming pulse 34, as shown in FIG. 5b. Typically this change is on the order of 2V, and this signal decays exponentially towards a level of 100 mV due to the lower DC gain. The time constant for this exponential decay is about 0.25 second, and is determined by the resistor 36 and the capacitor 38.

Departure of test gas from the sample chamber causes a negative change in the signal on the conductor 32 of 2V from whatever value the signal had at the time. This is indicated by the negative swing 40 of the preamplifier output shown in FIG. 5b. Following this negative swing, the preamplifier signal decays toward the original quiescent level.

The output of the preamplifier on the conductor 32 is applied to the comparator 46 to produce an alarm signal in the following manner. The output of the comparator 46 will be in a HIGH state whenever the conductor 42 is at a higher voltage than the conductor 44. The voltage on the conductor 44 follows the level of the voltage on the conductor 32 but with a time constant filter of 4.7 seconds due to the resistor 48 and the capacitor 50.

Initially, the conductor 44 will be at the quiescent level, and when conductor 32 makes the positive swing 51 of FIG. 5b, the conductor 44 will also move higher at a rate proportional to the difference in voltage between conductor 32 and conductor 44; that is, fast at first, then diminishing, then following conductor 32 during the negative swing 40, and eventually decaying back to the quiescent level. The signal on the conductor 44 is shown by a dashed line in FIG. 5b.

The signal on the conductor 42 resembles that on the conductor 32 but is 20 mV lower due to the resistors 52 and 54, and also has a 5 mV hysteresis due to the resistor 56. Because of the hysteresis, in order for the comparator output on the conductor 58 to go to the HIGH state, the signal on the conductor 32 must have a quick change of greater than +25 mV, and the HIGH state will be maintained so long as the voltage on the conductor 42 exceeds that on the conductor 32 by 15 mV. This threshold discriminates against false alarm signals caused by small changes in gas concentration and by noise from the preamplifier and the detector. The resulting alarm output on the conductor 58 is shown in FIG. 5c. Note that there is no output when conductor 32 experiences the negative drop 40, because during that drop and its recovery, the signal on the conductor 42 remains less than the signal on the conductor 44.

In FIG. 5, the signal produced by the detector and shown in FIG. 5a is a pulse having a duration of approximately 0.5 seconds in the preferred embodiment. In contrast, the waveforms in FIG. 6 show what happens when the output of the detector is a longer pulse, greater than 1 second in duration in the preferred embodiment.

As shown in FIG. 6, the leading edge 60 of the incoming pulse shown in FIG. 6a produces the pulse 62 shown in FIG. 6c on the output conductor 58 in exactly the same manner as described above in connection with FIG. 5. The essential difference in FIG. 6 is that the trailing edge 64 of the incoming pulse of FIG. 6a occurs much later than in FIG. 5a, thereby giving the signal on the conductor 44, shown in the dashed line of FIG. 6b, sufficient time to return to the quiescent level before the occurrence of the trailing edge 64.

As shown in the right-hand portion of FIG. 6, occurrence of the trailing edge 64 of the input signal received from the detector causes the signal on the conductor 32 to experience a sharp negative swing 66. The time constant for the recovery 68 is approximately 0.25 seconds in the preferred embodiment. The sharp negative swing 66 also pulls the signal on the conductor 44 negative as shown in the dashed line of FIG. 6b; the time constant for changes in that signal is approximately 4.7 seconds in the preferred embodiment. As a result of the disparity in the time constants, the negative signal 68 on the conductor 42 returns to its quiescent level more rapidly than the signal on the conductor 44. Accordingly, at some time 70 the signal on the conductor 32 again exceeds the signal on the conductor 44 by an amount that exceeds the 25 mV threshold and 5 mV hysteresis level, and a second pulse 72 is produced on the conductor 58. That pulse continues until the difference between the signal on the conductor 32 and the signal on conductor 44 becomes less than 15 mV.

Reflecting on the operation of the circuit of FIG. 4, as explained through the use of FIGS. 5 and 6, it is seen that the use of the hysteresis effect causes the system to ignore slow increases in the concentration of the test gas as well as slow changes in detector sensitivity with temperature or changes in the lamp output with age. The system responds only to relatively rapid changes in concentration of the test gas such as occur when the sampling probe is moved past a leak. If the concentration of the test gas exceeds some threshold, at least one pulse will be produced on the conductor 58. If the change in concentration is large, resulting in a longer input signal from the detector, two pulses will be produced as the sampling probe is moved past the location of the leak. These characteristics have proven to be very helpful in determining the exact location of a leak by scanning a sample collecting probe over the surface of the chamber that is being tested.

Thus there has been described a system for detecting slow leaks through the wall of a chamber. The system is noteworthy for its high speed, low cost, and ease of use. These benefits result from the use of a nondispersive infrared (NDIR) detector to detect small concentrations of a test gas that may be present in an ambient gas. Maximum sensitivity is obtained through selection of both the test gas and the ambient gas so that the ambient gas does not absorb radiation at a wavelength coinciding with a strong absorption band of the test gas. As a result of this choice, the ambient gas is invisible to the detector, and the presence of test gas is not obscured by the simultaneous presence of ambient gas, even when the concentration of the ambient gas is far greater than the concentration of the test gas. Concentrations of test gas as low as one part per million can be measured.

A novel gas sampling probe has been described which permits use of a chosen ambient gas even when the chamber being tested is located in the air of the atmosphere.

Finally, a novel signal processing circuit permits the system to identify rapid changes in concentration of the test gas, such as occur when the gas sampling probe is moved past a leak. At the same time, the signal processing circuit ignores slow changes in the concentration of the test gas and slow changes in system parameters, thereby practically eliminating false alarms. The signal processing circuit also gives a rough indication of the magnitude of the concentration change, and this has proven to be very helpful to the user in locating the leak.

The foregoing detailed description is illustrative of one embodiment of the invention, and it is to be understood that additional embodiments thereof will be obvious to those skilled in the art. The embodiments described herein together with those additional embodiments are considered to be within the scope of the invention.

What is claimed is:

1. A leak locator for locating a leak from a chamber, comprising: means for introducing a test gas under pressure into the chamber until the total pressure inside the chamber exceeds atmospheric pressure;

means for supplying an atmosphere of an ambient gas adjacent a region on the surface of the chamber, wherein the test gas and the ambient gas have been chosen so that the test gas can be detected in low concentrations when mixed with the ambient gas;

a gas sampling probe adapted for capturing a gas sample at atmospheric pressure and including a housing;

a gas sample chamber located within the housing of said gas sampling probe and including a source of radiation and a detector of radiation, responsive to absorption of radiation passing through the captured gas sample to produce a signal representative of the concentration of a test gas present in the captured gas sample;

means for drawing the captured gas sample into said gas sampling probe and through said gas sample chamber; and, signal processing means electrically connected to said detector of radiation for producing an alarm signal in response to changes in the concentration of the test gas.

2. A method for locating leaks from a chamber, comprising the steps of:
   a) identifying an ambient gas and selecting a test gas that can be detected in low concentrations when mixed with the ambient gas;
   b) introducing the test gas under pressure into the chamber until the total pressure inside the chamber exceeds ambient pressure;
   c) disposing the chamber in the selected ambient gas;
   d) obtaining a sample of gas from a small region adjacent the surface of the chamber;
   e) introducing the sample of gas into the gas sample chamber of an NDIR gas sensor;
   f) passing radiation through the sample of gas, said radiation having a wavelength equal to a wavelength at which the test gas absorbs radiation; and,
   g) measuring the absorption of the radiation that results from its passage through the sample of gas.

3. A method for locating leaks from a chamber, comprising the steps of:
   a) identifying an ambient gas and selecting a test gas that can be detected in low concentrations when mixed with the ambient gas;
   b) introducing the test gas under pressure into the chamber until the total pressure inside the chamber exceeds ambient pressure;
   c) supplying an atmosphere of the ambient gas adjacent a small region on the surface of the chamber;
   d) obtaining a sample of gas from within the atmosphere of ambient gas adjacent a small region on the surface of the chamber;
   e) introducing the sample of gas into the gas sample chamber of an NDIR gas sensor;
   f) passing radiation through the sample of gas, said radiation having a wavelength equal to a wavelength at which the test gas absorbs radiation; and,
   g) measuring the absorption of the radiation that results from its passage through the sample of gas.

* * * * *